United States Patent
Natsoulis et al.

(12)

(10) Patent No.: US 6,207,457 B1
(45) Date of Patent: *Mar. 27, 2001

(54) TARGETED NUCLEOTIDE SEQUENCE DELIVERY AND INTEGRATION SYSTEM

(75) Inventors: Georges Natsoulis, Berkeley; Richard T. Surosky, Oakland, both of CA (US)

(73) Assignee: Avigen, Inc., Alameda, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/525,866

(22) Filed: Sep. 8, 1995

(51) Int. Cl.[7] ........................ C12N 15/87; C12N 15/00; A61K 48/00
(52) U.S. Cl. ................. 435/463; 424/93.2; 435/320.1; 435/455; 514/44
(58) Field of Search .......................... 514/44; 424/93.1; 435/320.1, 172.3, 371, 69.1, 325, 455, 463; 536/23.1

(56) References Cited

U.S. PATENT DOCUMENTS

| 5,475,745 | * | 12/1995 | Samulski et al. | 435/320.1 |
| 5,866,696 | * | 2/1999 | Carter et al. | 536/23.5 |
| 5,989,540 | * | 11/1999 | Carter et al. | 424/93.2 |
| 6,033,885 | * | 3/2000 | Latta et al. | 435/455 |

FOREIGN PATENT DOCUMENTS

| 0 592 836 A1 | | 4/1994 | (EP) . |
| 2716893 | | 9/1995 | (FR) . |
| WO 94/13788 | | 6/1994 | (WO) . |
| WO 95/06743 | | 3/1995 | (WO) . |
| WO95/ 20671 | * | 8/1995 | (WO) . |
| WO 96/13598 | | 5/1996 | (WO) . |
| WO 96/15777 | | 5/1996 | (WO) . |

OTHER PUBLICATIONS

Gottlieb et al., "In Vitro Excision of Adeno–Associated Virus DNA from Recombinant Plasmids: Isolation of an Enzyme Fraction from HeLa Cells that Cleaves DNA at Poly(G) Sequences," *Molecular and Cellular Biol.* 6(8):2513–2522 (1988).

Kotin et al., "Characterization of a Preferred Site on Human Chromosome 19q for Integration of Adeno–associated Virus DNA by Non–homologous Recombination," *The EMBO Jrnl.* 11(13):5071–5078 (1992).

Kotin, "Prospects for the Use of Adeno–Associated Virus as a Vector for Human Gene Therapy," *Human Gene Therapy* 5:793–801 (1994).

Lebkowski et al., "Adeno–Associated Virus: a Vector System for Efficient Introduction and Integration of DNA into a Variety of Mammalian Cell Types," *Molecular and Cellular Biol.*, 8(10):3988–3996 (1988).

Shelling et al., "Targeted Integration of Transfected and Infected Adeno–associated Virus Vectors Containing the Neomycin Resistance Gene," 1:165–169 (1994).

Weitzman et al., "Adeno–associated Virus (AAV) Rep Proteins Mediate Complex Formation between AAV DNA and its Integration Site in Human DNA," *Proc. Natl. Acad. Sci. USA* 91:5808–5812 (1994).

Batchu et al., "The trans–inhibitory Rep78 protein of adeno–associated virus binds to TAR region DNA of the human immunodeficiency virus type 1 long terminal repeat," *FEBS Letters* (1995)367(3):267–271.*

Nahreini et al., "Cloning and integration of DNA fragments in human cells via the inverted terminal repeats of the adeno–associated virus 2 genome," *Gene* (1992) 119(2):265–272.*

Natsoulis et al., "A system for specifically targeting genes to chromosome, " *Blood* (1995) 86(10)(1):236a.*

Urcelay et al., "Asymmetric replication in vitro from a human sequence element is dependent on adeno–associated virus rep protein," *Jrnl. of Virology* (1995)69(4):2038–2046.*

Philip, et al. Efficient and sustained gene expression in primary T lymphocytes and primary and cultured tumor cells mediated by adeno–associated virus plasmid DNA complexed to catoinic liposomes. Mol. Cell. Biol. 14:2411–2418, Apr. 1, 1994.*

* cited by examiner

*Primary Examiner*—John L. LeGuyader
*Assistant Examiner*—Dave Trong Nguyen
(74) *Attorney, Agent, or Firm*—Robins & Associates (57) ABSTRACT

A novel targeted nucleotide sequence delivery and integration system is provided. The integration system employs nucleic acid constructs having a targeting sequence capable of binding AAV Rep and a heterologous nucleotide sequence arranged relative to the targeting sequence such that the targeting sequence is capable of directing the integration of the heterologous sequence into a target site in a recipient genome. The system further employs Rep expression products which provide integration functions effective to mediate the site-specific integration of the targeting sequence and the heterologous sequence into the recipient genome. Methods are described, whereby the nucleotide sequence integration system can deliver and efficiently integrate large nucleotide sequences into target sites in recipient cell genomes. Therapeutic methods are also provided, wherein the integration systems are used to insert various therapeutically relevant nucleotide sequences into selected cells from a subject.

17 Claims, 3 Drawing Sheets

TARGETED NUCLEOTIDE SEQUENCE DELIVERY AND INTEGRATION SYSTEM

DESCRIPTION

1. Technical Field

The present invention relates generally to methods and compositions for nucleotide sequence delivery. More particularly, the invention relates to vector systems for use in gene delivery and which provide for targeting and integration of a selected nucleotide sequence into a recipient genome.

2. Background of the Invention

Gene delivery is a promising method for the treatment of acquired and inherited diseases. A number of viral based systems for gene transfer purposes have been described, such as retroviral systems which are currently the most widely used viral vector systems for this purpose. For descriptions of various retroviral systems, see, e.g., U.S. Pat. No. 5,219,740; Miller and Rosman (1989) *BioTechniques* 7:980–990; Miller, A. D. (1990) *Human Gene Therapy* 1:5–14; Scarpa et al. (1991) *Virology* 180:849–852; Burns et al. (1993) *Proc. Natl. Acad. Sci. USA* 90:8033–8037; and Boris-Lawrie and Temin (1993) *Cur. Opin. Genet. Develop.* 3:102–109.

Retroviral-based systems offer the desirable features of being able to enter suitable host cells and integrate themselves into the host genome, thereby inserting a gene of interest into the host genome. However, retroviral vector systems suffer from several drawbacks. In particular, retroviral particles are relatively labile and hence unstable. Therefore, purification of recombinant viruses can lead to significant loss in titer. Retroviruses also have a limited host range and are unable to integrate into nonreplicating cells. Accordingly, cells which do not normally divide, such as mature neurons, or cells which replicate slowly, cannot be genetically altered using retroviral vectors unless stimulated to divide before infection. Additionally, and importantly, retroviruses are known to cause disease in certain animals, including humans, and thus pose a significant health risk when used in gene delivery methods. Finally, retrovirus vectors integrate into the host cell chromosome randomly, which may cause insertional mutagenesis by activating oncogenes or inactivating tumor suppressor genes.

A number of adenovirus based systems have also been developed for gene delivery. Human adenoviruses are double-stranded DNA viruses which enter cells by receptor-mediated endocytosis. These viruses are particularly well suited for gene transfer because they are easy to grow and manipulate and they exhibit a broad host range in vivo and in vitro. Adenoviruses are also able to infect quiescent as well as replicating target cells. Adenovirus is easily produced at high titers and is stable so that it can be purified and stored. Even in the replication-competent form, adenoviruses cause only low level morbidity and are not associated with human malignancies. A number of adenovirus-based gene delivery systems have been described. See, e.g., Haj-Ahmad and Graham (1986) *J. Virol.* 57:267–274; Bett et al. (1993) *J. Virol.* 67:5911–5921; Mittereder et al. (1994) *Human Gene Therapy* 5:717–729; Seth et al. (1994) *J. Virol.* 68:933–940; Barr et al. (1994) *Gene Therapy* 1:51–58; Berkner, K. L. (1988) *BioTechniques* 6:616–629; Rich et al. (1993) *Human Gene Therapy* 4:461–476.

However, despite their advantages, adenovirus-based systems suffer from several drawbacks. Particularly, adenovirus vectors do not integrate their genetic material into the host genome and are thus only able to express proteins transiently in a host cell. Hence, as the host cells divide, the transferred gene is lost, giving rise to the need for repeated treatments when long term gene therapy is desired. Furthermore, adenovirus vectors express viral proteins that may elicit an immune response in a host, thereby decreasing the life of a transduced cell. This immunogenicity may also preclude subsequent treatments because of humoral and/or cellular immune responses by the host organism.

Adeno-associated virus (AAV) systems have also been used for gene delivery. AAV is a helper-dependent DNA parvovirus which belongs to the genus Dependovirus. AAV requires co-infection with an unrelated helper virus, either adenovirus, a herpesvirus or vaccinia, in order for a productive infection to occur. In the absence of such co-infection, AAV establishes a latent state by insertion of its genome into a host cell chromosome. AAV has a wide host range and is able to replicate in cells from any species so long as there is also a successful co-infection of such cells with a suitable helper virus. Thus, for example, human AAV will replicate in canine cells co-infected with a canine adenovirus. AAV has not been associated with any human or animal disease and does not appear to alter the biological properties of the host cell upon integration. Furthermore, integration of AAV into a host genome occurs at high frequency and is independent of cell replication. AAV particles are also relatively stable, and are known to be refractive to common physical purification techniques such as sonication and heat. For a detailed review of AAV, see Berns and Bohenzky (1987) *Advances in Virus Research* (Academic Press, Inc.) 32:243–307.

The AAV genome is composed of a linear, single-stranded DNA molecule which contains 4681 bases (Berns and Bohenzky, supra). The genome includes inverted terminal repeats (ITRs) at each end which function in cis as origins of DNA replication and as packaging signals for the virus. The ITRs are approximately 145 bp in length. The internal nonrepeated portion of the genome includes two large open reading frames, known as the AAV rep and cap regions, respectively. These regions code for the viral proteins involved in replication and packaging of the virion. In particular, a family of at least four viral proteins are synthesized from the AAV rep region, Rep 78, Rep 68, Rep 52 and Rep 40, named according to their apparent molecular weight. The AAV cap region encodes at least three proteins, VP1, VP2 and VP3. For a detailed description of the AAV genome, see, e.g., Muzyczka, N. (1992) *Current Topics in Microbiol. and Immunol.* 158:97–129.

AAV is unique among eukaryotic viruses in that it is able to integrate site-specifically into the genome of host cells. Particularly, it is now known that the AAV integration locus (termed "AAVS1") is human chromosome 19q13.3-qter. Samulski et al. (1991) *EMBO J.* 10:3941–3950; Kotin et al. (1992) *EMBO J.* 11:5071–5078. The AAVS1 region of chromosome 19 has been isolated, partially characterized and sequenced. See, Kotin et al. (1992), supra; Kotin et al. (1991) *Genomics* 10:831–834; and Kotin et al. (1990) *Proc. Natl. Acad. Sci. USA* 87:2211–2215. Further, AAV Rep recognition sequences have been identified on human chromosome 19 near sites of viral integration in AAVS1, and those sequences have been shown to have a repeating nucleotide motif similar to sequences within AAV ITRs that are also believed to be recognized by Rep. Weitzman et al. (1994) *Proc. Natl. Acad. Sci. USA* 91:5808–5812.

Characteristics of AAV, such as the ability to integrate into a host cell genome, nonpathogenicity, and particle stability, have elicited an interest in the art to provide AAV-based vector systems for use in gene delivery. A number of recombinant AAV vectors have been described. See generally, U.S. Pat. Nos. 5,173,414 and 5,139,941; International Publication Numbers WO 92/01070 (published Jan. 23, 1992) and WO 93/03769 (published Mar. 4, 1993); Lebkowski et al. (1988) *Molec. Cell. Biol.* 8:3988–3996; Vincent et al. (1990) *Vaccines* 90 (Cold Spring Harbor Laboratory Press); Carter, B. J. (1992) *Current opinion in Biotechnology* 3:533–539; and Kotin, R. M. (1994) *Human Gene Therapy* 5:793–801.

Recombinant AAV (rAAV) virions are produced in a suitable host cell which has been transfected with both an AAV helper plasmid and an AAV vector. See, e.g., U.S. Pat. No. 5,436,146 to Shenk et al.; and International Publication Nos. WO 95/13392, published May 18, 1995 and WO 95/13365, published May 18, 1995. An AAV helper plasmid generally includes AAV rep and cap coding regions, but lacks AAV ITRs. Accordingly, the helper plasmid can neither replicate nor package itself. An AAV vector generally includes a selected gene of interest bounded both 5' and 3' by AAV ITRs which provide for viral replication and packaging functions. The 3' and 5' ITRs are necessary for packaging the bounded gene of interest into recombinant AAV particles. Both the helper plasmid and the AAV vector bearing the selected gene are introduced into a suitable host cell by transient transfection. The transfected cell is then infected with a helper virus, such as an adenovirus, which transactivates the AAV promoters present on the helper plasmid that direct the transcription and translation of AAV rep and cap regions. Recombinant AAV virions harboring the selected gene are formed and can be purified from the preparation.

The successful integration of AAV-based vectors into a host genome is dependent on the presence of functional ITR sequences, thus, the remainder of the AAV genome is deemed to be dispensable, and can be replaced by foreign DNA for use in gene delivery. However, without rep coding sequences, AAV vectors do not integrate in a site-specific manner into a host cell genome. Thus, only AAV vectors having the AAV rep coding region positioned between flanking ITRs have been able to successfully integrate into chromosome 19. Shelling et al. (1994) *Gene Therapy* 1:165–169. Such vectors are of limited value, though, as AAV vectors containing rep coding sequences between flanking ITRs will insert the rep gene into the host cell genome, resulting in expression of viral genes. Further, such vectors increase the potential for wild type virus generation, and the size of genetic material that can be packaged along with the rep coding sequence is greatly limited.

Accordingly, even though recombinant AAV virions have a number of desirable attributes, AAV-based gene delivery systems suffer from several serious drawbacks. Recombinant AAV virions integrate into the genome of the host cell, but not in a site-specific manner. Production methods are inherently labor-intensive and inefficient, relying on multiple transfections, and it is difficult to produce recombinant virus stocks that are free from contaminating wild-type AAV. In this regard, the presence of wild-type AAV particles in AAV-based vector systems could potentially lead to unintentional spread of recombinant AAV virions, and may interfere with the efficient expression of foreign genes. AAV-based vector systems are also inherently limited by the size constraint imposed by the inability of DNA fragments larger than about 5 kilobases (kb) to be packaged into mature AAV particles. Thus, gene sequences of interest that are larger than about 5 kb cannot be delivered using recombinant AAV vector systems.

It would thus be desirable to provide a nucleotide sequence integration system that is capable of providing the site-specific integration characteristics of AAV, is not limiting in regard to the size of the nucleotide sequence that can be delivered, and does not result in the integration of viral gene sequences into the recipient cell genome. It would also be desirable to provide a nucleotide sequence integration system that can be produced without the concomitant production of contaminating wild-type virions. Such a system could be used to safely and efficiently deliver and integrate large nucleotide sequences into a suitable recipient cell genome without the risk of causing insertional mutagenesis due to random integration events. Stable integration of the nucleotide sequence into the host genome can provide for long-term gene therapy. Accordingly, there remains a need to provide such improved nucleotide sequence delivery and integration systems.

SUMMARY OF THE INVENTION

The present invention provides for novel systems for use in nucleotide sequence delivery and integration. In particular, vector delivery systems are described which provide for site-specific targeting and efficient integration of a selected nucleotide sequence into a recipient genome. Integration can be targeted to a defined and benign genomic site, thereby reducing the risk of insertional mutagenesis which can occur with viruses which integrate randomly, while concomitantly increasing the predictability of gene expression. The selected nucleotide sequence to be integrated is not limited by size as in previous systems, since the present systems are not packaged in AAV virions.

The nucleotide sequence delivery systems of the invention generally include two components. First, a nucleic acid construct is provided having at least one nucleotide sequence of interest with an associated targeting sequence that is capable of binding AAV Rep. The targeting sequence is arranged in the construct relative to the nucleotide sequence of interest such that it is able to direct the integration of the nucleotide sequence of interest into a specific target site in a recipient cell genome.

The nucleotide sequence delivery systems also include a source of Rep expression products. The Rep expression products cooperate with the targeting sequence present in the first construct to effect the site-specific integration of the associated nucleotide sequence of interest into a recipient cell genome. The subject system has a broad host range and can be used to introduce nucleotide sequences into quiescent as well as replicating recipient cells. Furthermore, the system is safe and does not cause human diseases or cancers.

Accordingly, in one embodiment, a nucleotide sequence integration system capable of inserting a selected nucleotide sequence into a suitable recipient cell genome is provided. The integration system features a vector comprising a first nucleic acid construct having a targeting sequence that is capable of binding AAV Rep and at least one associated heterologous nucleotide sequence. The nucleotide integration system also features a second nucleic acid construct comprising an AAV rep coding sequence that is capable of being expressed in the recipient cell, thereby providing rep translation products that effect the integration of the heterologous nucleotide sequence present in the first construct into the genome of the recipient cell when the integration system has been introduced into the recipient cell.

In related aspects of the invention, the above nucleotide sequence integration systems are assembled such that the first and second nucleic acid constructs are present in a single vector. The vector can be in the form of a circular piece of DNA such as, but not limited to, a plasmid or a cosmid. In further related aspects, the targeting sequence in the first nucleic acid construct is homologous to a single inverted terminal repeat (ITR) sequence. In one particular system, the target sequence is substantially homologous to a wild type (wt) AAV ITR sequence.

In another embodiment, the invention is directed to methods of integrating a selected nucleotide sequence into a recipient cell genome. Such methods generally comprise the steps of: (a) introducing a first nucleic acid construct into the recipient cell, wherein the first construct comprises a targeting sequence that is capable of binding AAV Rep and a selected heterologous nucleotide sequence suitably arranged in the construct relative to the targeting sequence whereby the targeting sequence is capable of directing the integration of the selected sequence into a target site in the recipient cell genome; and (b) introducing a second nucleic acid construct into the recipient cell, wherein the second construct comprises an AAV rep coding region operably linked to control elements capable of directing the transcription and translation of the rep coding region in the recipient cell.

In related aspects of the invention, the above methods entail the co-transfection of a suitable recipient cell with the first and second nucleic acid constructs. In other aspects, the first and second nucleic acid constructs are provided in a nucleotide sequence integration system that has been constructed according to the present invention. The first and second constructs can further be present in a single vector, such as in a plasmid or a cosmid. In yet further related aspects of the invention, the targeting sequence is substantially homologous to a wt AAV ITR sequence. In one particular method, the selected nucleotide sequence is integrated into chromosome 19 of the recipient cell genome.

In each of the above methods, the nucleotide sequence delivered into the recipient cell genome can comprise a coding region that encodes a polypeptide, wherein the coding region is operably linked to control elements capable of directing the transcription and translation of that region in a suitable recipient cell. In further related methods, the coding region encodes a protein that is either defective or missing from the recipient cell genome. In other methods, the coding region is capable of over-expressing a protein encoded by the recipient cell genome. In yet further related methods, the coding region encodes a protein having an antiviral function.

In yet additional embodiments, the invention is directed to methods of treating an acquired or inherited disease in a subject, which methods generally comprise transforming a selected recipient cell from the subject with a nucleotide sequence integration system constructed in accordance with the present invention. In this manner, rep translation products provided by the nucleotide sequence integration system effect the site-specific integration of a selected nucleotide sequence into the genome of the recipient cell.

These and other embodiments of the subject invention will readily occur to those of ordinary skill in the art in view of the disclosure herein.

DETAILED DESCRIPTION OF THE INVENTION

The practice of the present invention will employ, unless otherwise indicated, conventional methods of virology, microbiology, molecular biology and recombinant DNA techniques within the skill of the art. Such techniques are explained fully in the literature. See, e.g., Sambrook, et al. *Molecular Cloning: A Laboratory Manual* (Current Edition); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *CRC Handbook of Parvoviruses*, vol. I & II (P. Tijessen, ed.); *Fundamental Virology*, 2nd Edition, vol. I & II (B. N. Fields and D. M. Knipe, eds.)

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

"Gene transfer" or "gene delivery" refers to methods or systems for reliably inserting a particular nucleotide sequence (e.g., DNA) into targeted cells. Such methods preferably result in the integration of the transferred genetic material into the genome of target cells. Gene transfer provides a unique approach for the treatment of acquired and inherited diseases, and a number of systems have been developed in the art for gene transfer into mammalian cells. See, e.g., U.S. Pat. No. 5,399,346.

By "adeno-associated virus inverted terminal repeats," "AAV ITRs," or "ITRs" is meant the art-recognized, approximately 145-bp palindromic nucleotide regions found at each end of the AAV genome which function together in cis as origins of DNA replication and as packaging signals for the virus. More particularly, AAV ITRs are composed of three palindromic sequences, denoted "A," "B" and "C," which fold into a hairpin T-shaped structure in replicating AAV DNA. Lusby et al. (1980) *J. Virol.* 34:402–409; Straus et al. (1976) *Proc. Natl. Acad. Sci. USA* 73:742–746. A single 3' non-palindromic region, comprising 20 nucleotides and denoted "D," completes the 145-bp ITR sequence, and is thought to also participate in AAV DNA replication. The two long-form AAV rep-encoded polypeptides, Rep78 and Rep68, bind to AAV ITRs in the hairpin configuration (Snyder et al. (1993) *J. Virol.* 67:6096–6104 and Ashktorab et al. (1989) *J. Virol.* 63:3034–3039), and participate in a replication process denoted terminal resolution. Snyder et al. (1990) *Cell* 60:105–113. Recent studies have shown that the Rep78 and Rep68 proteins are also able to recognize and bind a linear DNA sequence that is contained within a 25-base sequence of the A stem of the AAV ITR that is proximal to the B and C palindromes. McCarty et al. (1994a) *J. Virol.* 68:4988–4997; McCarty et al. (1994b) *J. Virol.* 68:4998–5006. The Rep binding site in the AAV ITR has been further characterized as a 12-base nucleotide sequence that is similar to a GCTC repeating motif found at or near the AAV integration site (termed "AAVS1") present in 19q13-qter. Weitzman et al. (1994) *Proc. Natl. Acad. Sci. USA* 91:5808–5812; Shelling et al. (1994) *Gene Therapy* 1:165–169. Thus, the Rep binding site in AAV ITRs is deemed necessary for the target-specific integration of AAV into AAVS1.

For the purpose of the present invention, a single AAV ITR is positioned relative to one or more selected heterologous nucleotide sequences and, together with an expressible AAV rep coding region or Rep expression products, can provide for the integration of the associated sequences into the genome of a target cell. The nucleotide sequences of AAV ITR regions are known. See, e.g., Kotin, R. M. (1994) *Human Gene Therapy* 5:793–801; Berns, K. I. "Parvoviridae and their Replication" in *Fundamental Virology*, 2nd Edition, (B. N. Fields and D. M. Knipe, eds.), see FIG. 1 (SEQ. ID No. 1) for the AAV-2 sequence. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAVX7, etc. However, the term "AAV ITR" as used herein denotes a nucleotide sequence having not more than one region that is substantially homologous to the 20 base "D" region found in wild-type AAV ITR sequences. The AAV ITR sequence need only function as intended, i.e., to allow for the integration of the associated heterologous sequence into the recipient cell genome when an expressible AAV rep coding region is present (either on the same or on a different vector), or when Rep expression products have also been introduced into the recipient cell.

The term "targeting sequence" is defined herein to encompass any polynucleotide sequence that is capable of binding AAV Rep expression products, whereby the Rep expression products mediate the integration of the targeting sequence along with an associated nucleotide sequence into a suitable recipient cell genome. In this way, the targeting sequence—in conjunction with the integration functions provided by the Rep expression products—is capable of preferentially integrating, along with an associated nucleotide sequence, into the human genome at a site on chromosome 19, particularly the AAVS1 site of 19q13-qter. For example, an ITR sequence, or fragment thereof, which is capable of binding Rep and being inserted into a recipient cell genome is encompassed by the term "target sequence."

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

By a "nucleotide sequence integration vector" is meant a vector comprising a nucleic acid construct which includes a targeting sequence as defined herein and an associated heterologous nucleotide sequence. For example, if an ITR sequence is employed as the targeting sequence, it need not be a wild-type ITR sequence, and may be altered, e.g., by the insertion, deletion or substitution of nucleotides, so long as the ITR is capable of directing the integration of the associated nucleotide sequence into the genome of a recipient host.

Nucleotide sequence integration vectors can be constructed using recombinant techniques that are known in the art to include one or more heterologous nucleotide sequences associated with a functional AAV ITR sequence or other suitable targeting sequence. In the practice of the invention, a nucleotide sequence integration vector can include a single AAV ITR and a suitable promoter sequence positioned upstream of the heterologous nucleotide sequence.

Nucleotide sequence integration vectors can also include transcription sequences such as polyadenylation sites, as well as selectable markers or reporter genes, enhancer sequences, and other control elements which allow for the induction of transcription. Such control elements are described more fully below.

Suitable nucleotide sequences for use in nucleotide sequence integration vectors include any functionally relevant nucleotide sequence. Thus, the vectors of the present invention can comprise any desired gene that encodes a protein that is defective or missing from a recipient cell genome or that encodes a non-native protein having a desired biological or therapeutic effect (e.g., an antiviral function), or the sequence can correspond to a molecule having an antisense or ribozyme function. Suitable genes include those used for the treatment of inflammatory diseases, autoimmune, chronic and infectious diseases, including such disorders as AIDS, cancer, neurological diseases, cardiovascular disease, hypercholestemia; various blood disorders including various anemias, thalasemias and hemophilia; genetic defects such as cystic fibrosis, Gaucher's Disease, adenosine deaminase (ADA) deficiency, emphysema, etc. A number of antisense oligonucleotides (e.g., short oligonucleotides complementary to sequences around the translational initiation site (AUG codon) of an mRNA) that are useful in antisense therapy for cancer and for viral diseases have been described in the art. See, e.g., Han et al. (1991) *Proc. Natl. Acad. Sci. USA* 88:4313–4317; Uhlmann et al. (1990) *Chem. Rev.* 90:543–584; Helene et al. (1990) *Biochim. Biophys. Acta.* 1049:99–125; Agarwal et al. (1988) *Proc. Natl. Acad. Sci. USA* 85:7079–7083; and Heikkila et al. (1987) *Nature* 328:445–449. For a discussion of suitable ribozymes, see, e.g., Cech et al. (1992) *J. Biol. Chem.* 267:17479–17482 and U.S. Pat. No. 5,225,347 to Goldberg et al.

By "recombinant virus" is meant a virus that has been genetically altered, e.g., by the addition or insertion of a heterologous nucleic acid construct into the particle.

By "AAV rep coding region" is meant the art-recognized region of the AAV genome which encodes the replication proteins of the virus which are collectively required for replicating the viral genome and for insertion of the viral genome into a host genome during latent infection, or functional homologues thereof such as the human herpesvirus 6 (HHV-6) rep gene which is also known to mediate AAV-2 DNA replication (Thomson et al. (1994) *Virology* 204:304–311). Thus, the rep coding region includes at least the genes encoding for AAV Rep 78 and Rep 68 (the "long forms of Rep"), and Rep 52 and Rep 40 (the "short forms of Rep"), or functional homologues thereof. For a further description of the AAV rep coding region, see, e.g., Muzyczka, N. (1992) *Current Topics in Microbiol. and Immunol.* 158:97–129; and Kotin, R. M. (1994) *Human Gene Therapy* 5:793–801. The rep coding region, as used herein, can be derived from any viral serotype, such as the AAV serotypes described above. The region need not include all of the wild-type genes but may be altered, e.g., by the insertion, deletion or substitution of nucleotides, so long as the rep genes present provide for sufficient integration functions when expressed in a suitable recipient cell.

"Rep expression products" are defined herein to include those AAV rep transcription products that are necessary and sufficient to supply integration functions in a recipient cell. In this regard, both the short forms and the long forms of AAV Rep, including functional homologous thereof, are encompassed by the definition.

As used herein, the terms "integration" and "nucleotide sequence integration" encompass the insertion of a nucleotide sequence, i.e., a DNA sequence, into a larger, normally genomic, recipient sequence or sequences. Such insertion of viral and/or heterologous nucleotide sequences into a recipient sequence is generally accomplished by recombination events, whereby the inserted nucleotide sequence becomes covalently incorporated into the recipient sequence or sequences. "Integration functions" refer to the ability of one or more polypeptides to mediate the integration of a nucleotide sequence into a recipient sequence or sequences, preferably in a site-directed manner.

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) *Virology,* 52:456, Sambrook et al. (1989) *Molecular Cloning, a laboratory manual,* Cold Spring Harbor Laboratories, New York, Davis et al. (1986) *Basic Methods in Molecular Biology,* Elsevier, and Chu et al. (1981) *Gene* 13:197. Such techniques can be used to introduce one or more exogenous DNA moieties, such as a nucleotide integration vector and other nucleic acid molecules, into suitable host cells.

As used herein, a "nucleotide sequence integration system" intends the operative combination of: (1) a first nucleic acid construct, comprising a targeting sequence capable of binding AAV Rep, and at least one heterologous nucleotide sequence of interest arranged relative to the targeting sequence such that the targeting sequence is capable of directing the integration of the heterologous sequence into a target site in a recipient cell genome, i.e., the targeting sequence can be positioned 3' or 5' relative to the heterologous sequence; and (2) either a further nucleic acid construct having a rep coding region operably linked to control elements capable of directing the transcription and translation of the rep coding region in a suitable recipient cell, or a suitable amount of Rep expression products, whereby the nucleotide sequence integration system provides for the integration of the nucleotide sequence of interest from the first construct into the genome of a recipient cell that has been transfected with the integration system.

By "recipient cell," or "recipient mammalian cell" is meant a cell which has been transformed, or is capable of transformation, by a nucleic acid construct or a nucleotide sequence integration vector bearing a selected nucleotide sequence of interest. The term includes the progeny of the parent cell, whether or not the progeny is identical in morphology or in genetic make-up to the original parent, so long as the selected nucleotide sequence is present.

A recipient cell has been "stably transformed" with a nucleic acid construct comprising a selected nucleotide sequence of interest when the construct has been introduced inside the cell membrane and the sequence of interest has integrated into the recipient cell genome such that it is capable of being inherited by daughter cells through chromosome replication. The recipient cell can be transformed using any of several techniques, including transduction, transfection and infection. Stability is demonstrated by the ability of the recipient cell to establish cell lines or clones comprised of a population of daughter cells which contain the nucleotide sequence of interest.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "coding sequence" or a sequence which "encodes" a particular protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

A "nucleic acid" sequence refers to a DNA or RNA sequence. The term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

By "isolated" when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3'," or "5'" relative to another sequence, it is to be understood that it is the position of the sequences in the "sense" or "coding" strand of a DNA molecule that is being referred to as is conventional in the art.

"Homology" refers to the percent of identity between two polynucleotide or two polypeptide moieties. The correspondence between the sequence from one moiety to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single-stranded-specific nuclease(s), and size determination of the digested fragments. Two DNA, or two polypeptide sequences are "substantially homologous" to each other when at least about 80%, preferably at least about 90%, and most preferably at least about 95% of the nucleotides or amino acids match over a defined length of the molecules, as determined using the methods above.

A "functional homologue," or a "functional equivalent" of a given polypeptide includes molecules derived from the native polypeptide sequence, as well as recombinantly produced or chemically synthesized polypeptides which function in a manner similar to the reference molecule to achieve a desired result. Thus, a functional homologue of AAV Rep68 or Rep78 encompasses derivatives and analogues of those polypeptides—including any single or multiple amino acid additions, substitutions and/or deletions occurring internally or at the amino or carboxy termini thereof—so long as integration activity remains.

A "functional homologue," or a "functional equivalent" of a given AAV nucleotide region includes similar regions derived from a heterologous AAV serotype, as well as recombinantly produced or chemically synthesized polynucleotides which function in a manner similar to the reference nucleotide region to achieve a desired result. Thus, a functional homologue of an AAV ITR region encompasses derivatives and analogues of such sequences—including any single or multiple nucleotide base additions, substitutions and/or deletions occurring within the ITR region, so long as the ITR homologue retains the minimum number of bases or elements sufficient to mediate the integration thereof into a suitable host genome. A nucleotide sequence that is a functional homologue of an AAV ITR Rep binding site encompasses derivatives and analogues of the 12 base nucleotide sequence, synthetic or otherwise, so long as the sequence is capable of binding Rep expression products. Successful binding of Rep expression products to a nucleotide sequence can be determined using the mobility-shift assay described by Weitzman et al. (1994) Proc. Natl. Acad. Sci. USA 91:5808–5812.

B. General Methods

The present invention is based on the discovery that AAV Rep expression products can mediate the integration of a selected nucleotide sequence site-specifically into an appropriate recipient nucleotide sequence, so long as the selected nucleotide sequence contains a single target sequence capable of binding Rep. In this manner, the present invention provides, for the first time, a nucleotide sequence integration system that exhibits the site-specific integration characteristics of AAV without being limited in regard to the size of the nucleotide sequence that can be delivered. These novel systems can be used to safely and efficiently deliver and integrate large nucleotide sequences into a recipient genome to provide for predictable, long-term expression of the inserted nucleotide sequences.

Thus, it is a primary object of the invention to provide isolated nucleic acid constructs that contain a targeting sequence capable of binding AAV Rep, and at least one heterologous nucleotide sequence that has been suitably arranged in the construct relative to the targeting sequence whereby the targeting sequence is capable of directing the integration of the heterologous sequence into a target site in a suitable recipient cell genome.

Figure 1:
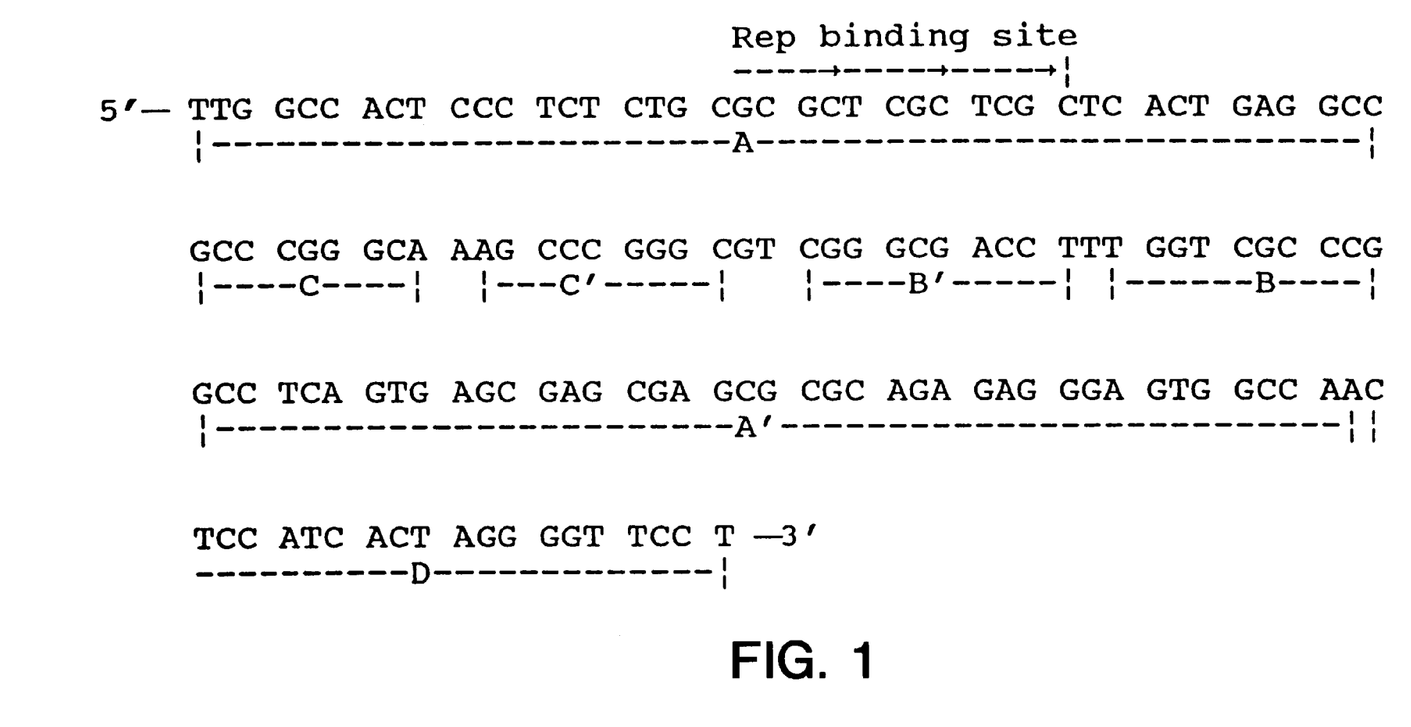
FIG. 1 (SEQ ID NO. 1) depicts the nucleotide sequence of an ITR from the wild type AAV serotype 2 genome, wherein the A, B, and C palindrome regions, the D region and the Rep binding site have been indicated.

More particularly, the targeting sequence of the subject nucleic acid constructs provides a binding site for AAV Rep expression products that is homologous to an AAV ITR Rep binding site. In this manner, AAV Rep expression products are capable of mediating the integration of the targeting sequence—along with any associated heterologous nucleotide sequence—into a recipient cell genome. Referring to FIG. 1, targeting sequences as used herein include at least one region that is functionally homologous to the 12 base Rep binding site found in wild-type AAV ITR sequences. See, e.g., Kotin, R. M. (1994) Human Gene Therapy 5:793–801. The Rep binding site contains sequences that are similar to a GCTC repeating motif found at or near the AAV integration site (termed "AAVS1") present in the human genome at 19q13-qter. Weitzman et al. (1994) Proc. Natl. Acad. Sci. USA 91:5808–5812; Shelling et al. (1994) Gene Therapy 1:165–169. Thus, AAV ITR Rep binding sites are deemed necessary for the target-specific integration of AAV into AAVS1.

The targeting site is arranged in the nucleic acid constructs of the invention either 3' or 5' relative to the selected heterologous sequence of interest, such that the targeting sequence and the heterologous sequence can be inserted into a recipient cell genome via Rep expression product-mediated integration functions. Thus, in preferred embodiments, the targeting sequence is capable of directing the integration of the heterologous sequence in a site-specific manner into a recipient genome, such as into AAVS1 of chromosome 19 in human recipient cells.

In one particular aspect of the invention, an isolated nucleic acid construct is provided having a targeting sequence that is homologous to a single AAV ITR sequence. As described above, AAV ITRs are approximately 145 base nucleotide sequences that comprise three palindromic sequences, denoted "A," "B" and "C" (Lusby et al. (1980) *J. Virol.* 34:402–409; Straus et al. (1976) *Proc. Natl. Acad. Sci. USA* 73:742–746), and a single 3' 20 nucleotide non-palindromic region denoted "D." Included in the ITR sequence is a functional Rep binding site as described above. Under the invention, the ITR sequence need not be a wild-type sequence, e.g., it can be altered such as by the insertion, deletion or substitution of nucleotides. The ITR can be synthetically derived using known methods, and/or the ITR may be derived from any of several AAV serotypes, including without limitation, AAV-1, AAV-2, AAV-3, AAV-4, AAV-5, AAVX7, etc. However, the ITR is selected so as to have not more than one region that is substantially homologous to the 20 base "D" region found in wild-type AAV ITR sequences. In one particular construct, the targeting sequence comprises the 145 base pair ITR sequence as depicted in FIG. 1 (SEQ ID NO: 1).

The subject nucleic acid constructs can be engineered using recombinant techniques known to those of skill in the art. In particular, an AAV ITR sequence can be excised from the viral genome or from an AAV vector plasmid containing the same and fused, either 5' or 3' of a selected nucleotide sequence which is present in another vector, using standard ligation techniques, such as those described in Sambrook et al., supra. For example, ligations can be accomplished in 20 mM Tris-Cl pH 7.5, 10 mM MgCl$_2$, 10 mM DTT, 33 ug/ml BSA, 10 mM–50 mM NaCl, and either 40 uM ATP, 0.01–0.02 (Weiss) units T4 DNA ligase at 0° C. (for "sticky end" ligation) or 1 mM ATP, 0.3–0.6 (weiss) units T4 DNA ligase at 14° C. (for "blunt end" ligation). Intermolecular "sticky end" ligations are usually performed at 30–100 $\mu$g/ml total DNA concentrations (5–100 nM total end concentration). AAV vectors which contain ITRs have been described in, e.g., U.S. Pat. No. 5,139,941 and are available from the American Type Culture Collection ("ATCC") under accession numbers 53222, 53223, 53224, 53225 and 53226.

Additionally, chimeric nucleotide sequences can be produced synthetically to provide AAV ITR sequence homologues, or suitable target sequences (containing functional Rep binding sites) and then fused 5' or 3' of the selected nucleotide sequence. AAV ITR nucleotide sequences are known. See, e.g., Kotin, R. M. (1994) *Human Gene Therapy* 5:793–801; and Berns, K. I. "Parvoviridae and their Replication" in *Fundamental Virology*, 2nd Edition, (B. N. Fields and D. M. Knipe, eds.), for the AAV-2 sequence. Preferred codons for expression of the chimeric nucleotide sequence in mammalian cells can be used. The complete chimeric sequence is assembled from overlapping oligonucleotides prepared by standard methods. See, e.g., Edge, *Nature* (1981) 292:756; Nambair et al. *Science* (1984) 223:1299; Jay et al. *J. Biol. Chem.* (1984) 259:6311.

The selected heterologous nucleotide sequence of the nucleic acid constructs of the invention can comprise any desired gene that encodes a protein that is defective or missing from a recipient cell genome or that encodes a non-native protein having a desired biological or therapeutic effect (e.g., an antiviral function), or the sequence can correspond to a molecule having an antisense or ribozyme function. Suitable genes include those used for the treatment of inflammatory diseases, autoimmune, chronic and infectious diseases, including such disorders as AIDS, cancer, neurological diseases, cardiovascular disease, hypercholestemia; various blood disorders including various anemias, thalasemias and hemophilia; genetic defects such as cystic fibrosis, Gaucher's Disease, adenosine deaminase (ADA) deficiency, emphysema, etc.

In one particular aspect of the invention, nucleic acid constructs are provided having a target sequence and an associated heterologous nucleotide sequence that comprises a coding region that is capable of encoding a polypeptide. The coding region can encode, for example, a protein that is defective or missing from a recipient cell genome. Nucleic acid constructs can also be supplied, wherein a selected coding region overexpresses an endogenous protein encoded by a recipient genome. Thus, constructs provided under the present invention are particularly useful in assembling gene transfer systems for use in gene delivery.

The coding region is operably linked to control elements that are capable of directing the transcription and translation thereof in a suitable recipient cell. Suitable control sequences can include promoter sequences, polyadenylation signals, transcription termination sequences, upstream regulatory domains, origins of replication, internal ribosome entry sites ("IRES"), enhancers, and the like.

It is also an object of the invention to provide vectors for integration of a selected nucleotide sequence into a recipient mammalian cell genome. More particularly, vectors are provided herein, comprising nucleic acid constructs which include a targeting sequence and at least one heterologous nucleotide sequence and which have been constructed according to the invention. Such vectors can be in the form of any genetic element, such as a plasmid, phage, transposon, cosmid, chromosome, virus, virion, etc., which is capable of replication when associated with the proper control elements and which can transfer gene sequences between cells. Particularly preferred vectors under the invention comprise circular pieces of DNA such as cosmids or plasmids.

In on particular aspect of the-invention, vectors are provided that comprise a nucleic acid construct as defined herein and a selectable marker. Selectable markers useful in the practice of the invention include genes which confer antibiotic resistance or sensitivity, impart color, or change the antigenic characteristics, when a suitable host cell transformed with such a vector is grown in an appropriate selective medium.

It is yet a further object of the invention to provide nucleotide sequence integration systems that are capable of inserting a selected nucleotide sequence into a suitable recipient cell genome. More particularly, the integration systems of the present invention are an operative combination of: (1) a vector comprising a nucleic acid construct that contains a targeting sequence capable of binding AAV Rep, and at least one heterologous nucleotide sequence of interest arranged relative to the targeting sequence such that the targeting sequence is capable of directing the integration of the heterologous sequence into a target site in a recipient cell genome; and (2) AAV Rep expression products, whereby the expression products are capable of mediating the integration of the heterologous nucleotide sequence of the vector into the target site of the recipient cell genome in conjunction with the targeting sequence.

The nucleotide sequence integration systems of the present invention are capable of providing the site-specific integration characteristics of AAV via the cooperation of the targeting sequence and the integration functions provided by the Rep expression products. Further, the present integration systems are capable of delivering large nucleotide sequences and mediating the integration thereof into a recipient cell genome, wherein the integrated sequences are much larger than heretofore possible. This feature is due to the fact that the present integration systems do not have to be packaged within a viral particle for delivery and integration as in prior systems. In this manner, the present integration systems also do not result in the integration of viral gene sequences into the recipient cell genome since no viral particles are included in the systems.

The ability to configure the nucleic acid constructs which contain the selected nucleotide sequences in the form of vectors (such as, but not limited to, cosmids or plasmids) avoids problems encountered in past viral-based gene delivery systems wherein those systems generally cannot be produced without the concomitant production of contaminating wild-type virions. The present nucleotide integration systems can thus be used to safely and efficiently deliver and integrate large nucleotide sequences into a suitable recipient cell genome without the risk of causing insertional mutagenesis due to random integration events, or of encountering undesirable viral side-effects.

Accordingly, in one aspect of the invention, integration systems are provided wherein a suitable amount of Rep expression products (that have been produced according to routine methods of protein expression) are coupled with a vector (that has been constructed as described above) to provide a system capable of site-specific integration of a selected nucleotide sequence from the vector into a recipient genome having an appropriate target site therein. In this regard, a suitable amount of Rep expression products is defined herein as that amount which is necessary and sufficient to supply integration functions in a recipient cell.

Rep expression products can be readily produced by chemical synthesis such as by solid phase peptide synthesis, using known amino acid sequences or amino acid sequences derived from the DNA sequences of the genes encoding the various Rep proteins. Such methods are known to those skilled in the art. In this regard, the rep coding region has been cloned and sequenced. See, e.g., Muzyczka, N. (1992) *Current Topics in Microbiol. and Immunol.* 158:97–129; and Kotin, R. M. (1994) *Human Gene Therapy* 5:793–801. Rep expression products can also be obtained from nuclear extracts of human 293 cells transfected with constructs containing the rep coding region under the control of a suitable promoter using known extraction and purification methods. Owens et al. (1993) *J. Virol.* 67:997–1005. Further, Rep expression products can be produced using any of a number of suitable vectors in other peptide expression systems. Numerous appropriate vectors are known to those of skill in the art, and the selection of a particular vector is a matter of choice. For example, insect cell expression systems can be used, and expression of Rep proteins in recombinant baculovirus-infected SF9 insect cells has been described in the art. See, e.g., McCarty et al. (1994) *J. Virol.* 68:4998–5006; McCarty et al. (1994) *J. Virol.* 68:4988–4997; Ni et al. (1994) *J. Virol.* 68:1128–1138.

In another aspect of the invention, integration systems are provided wherein the Rep expression products are supplied by a second nucleic acid construct having a rep coding region operably linked to control elements capable of directing the transcription and translation of the rep coding region in a suitable recipient cell. Such nucleic acid constructs can be assembled using methods known in the art and described above.

Particularly, the rep coding region can be obtained from the viral genome or from an AAV vector plasmid known to include the same. In this regard, a number of rep containing AAV vectors are known, including the several vectors described in, e.g., U.S. Pat. No. 5,139,941, having ATCC accession numbers 53222, 53223, 53224, 53225 and 53226. Similarly, methods of obtaining the HHV-6 homologue of AAV rep are described in Thomson et al. (1994) *Virology* 204:304–311.

The rep coding region is operably linked to control sequences that direct the transcription and translation thereof. Such control elements include one or more of promoters, polyadenylation signals, transcription termination sequences, upstream regulatory domains, replication sequences, enhancers, and the like, which collectively provide for the transcription and translation of the rep coding region when present in the recipient cell.

Useful promoter sequences include those derived from sequences encoding mammalian genes or viral genes. Examples include but are not limited to the homologous AAV promoters, the SV40 early promoter, mouse mammary tumor virus LTR promoter; adenovirus major late promoter (Ad MLP); a herpes simplex virus (HSV) promoter, a cytomegalovirus (CMV) promoter, a rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene.

Additionally, regulatory elements can be picked that allow for the controlled expression of the rep coding region in the recipient cell. Such elements are turned on in response to an appropriate effector. In this way, the Rep expression products can be provided when integration of the selected nucleotide sequence into the genome of the recipient cell is desired. Regulatory sequences are known to those of skill in the art, and include e.g., elements derived from the lac operator-repressor system (see, e.g., Hu and Davidson *Cell* (1987) 48:555–566), origins of replication including those derived from papovaviruses, such as the SV40 origin of replication (SV40Ori) for which the T antigen is the effector, as well as cellular origins of replication, such as the dihydrofolate reductase (DHFR) gene for which methotrexate is the effector. See, e.g. Urlaub et al. (1980) *Proc. Natl. Acad. Sci. USA* 77:4216–4220; Rungold et al. (1981) *J. Mol. and Appl. Genet.* 1:165–175.

In particular systems, the appropriate effector will be available in the recipient cell at the time that expression of the AAV rep coding region is desired. Systems for administering regulatory compounds are known in the art. See, e.g., International Publication No. WO 88/09809, McVey et al. (1989) *Mol. Cell. Biol.* 9:5525–5536; and Van Doren et al. (1984) *Mol. Cell. Biol.* 9:5525–5536.

The second nucleic acid construct which includes the AAV rep coding region may also include selectable markers, such as genes which confer antibiotic resistance or sensitivity, or impart color, or change the antigenic characteristics, as has been described above.

In one particular aspect of the invention, nucleotide integration systems as described herein can be engineered such that both the first and second nucleic acid constructs are present on a single vector. However, this particular configuration may not be preferred in those instances wherein it is desired to avoid insertion of viral sequences into a recipient genome.

It is a still further object of the invention to provide methods of integrating a selected nucleotide sequence into a recipient cell genome. The methods generally entail: (1) introducing a first nucleic acid construct into the recipient cell, the first construct comprising a targeting sequence that is capable of binding AAV Rep, and a selected heterologous nucleotide sequence suitably arranged in the first construct relative to the targeting sequence such that the targeting sequence is capable of directing the integration of the heterologous sequence into a target site in the recipient cell genome; and (2) introducing Rep expression products into the recipient cell, whereby the Rep expression products are capable of effecting the integration of the selected heterologous nucleotide sequence from the first nucleic acid construct into the recipient cell genome.

Such methods can be practiced using any of the nucleic acid constructs and/or vectors that have been constructed according to the present invention. In one particular aspect of the invention, the above-described methods are practiced using the nucleotide sequence integration systems provided herein.

In one particularly preferred method, the nucleotide sequence selected for integration into the recipient genome is arranged in a nucleic acid construct relative to a targeting sequence that is substantially homologous to a single, wild-type AAV ITR sequence. In this manner, the targeting sequence is capable of preferentially integrating, along with the associated nucleotide sequence of interest, into a recipient human cell genome at a site on chromosome 19, particularly the AAVS1 site of 19q13-qter.

Each of the present methods of integrating a selected nucleotide sequence into a recipient cell genome entails introducing genetic information along with Rep expression products into a suitable recipient cell, whereby selected nucleotide sequences of interest are site-specifically integrated into the recipient cell genome. Thus, once engineered and assembled, the present integration systems can be used directly to transform a selected recipient cell. In this regard, the cell to be transformed will depend on the purpose for gene transfer, e.g., the disease state being treated. For example, the nucleotide integration system of the present invention can be used to deliver and integrate nucleotide sequences into any nucleated cell including stem, progenitor and erythroid cells; as well as any of the various white blood cells such as lymphocytes, neutrophils, eosinophils, basophils, monocytes; tissue specific cells, such as those derived from lung, heart, kidney, liver, spleen, pancreatic tissue, connective tissue, muscle and bone tissue including osteocytes, gangliocytes, epithelial and endothelial cells, ependymal cells, reticuloendothelial cells, dendritic and neural cells, and the like.

Generally, recipient cells will be transformed with the nucleotide sequence integration system of the present invention either in vivo or ex vivo. If transformed ex vivo, the desired recipient cell type will be removed from the subject, transformed and reintroduced into the subject. In this regard, a number of methods are known in the art for transforming cells, including dextran-mediated transfection, calcium phosphate precipitation, polybrene mediated transfection, protoplast fusion, electroporation, encapsulation of the nucleic acid constructs in liposomes, and direct microinjection of the DNA into nuclei. Such systems are known in the art and have been described in e.g., Finney and Bishop (1993) *Science* 260:1524–1527. The transformed cells can be screened for those cells harboring the selected gene, using conventional techniques such as drug resistance screening, Southern blots and/or PCR.

If delivered in vivo, the nucleic acid constructs will be formulated into pharmaceutical compositions and will generally be administered parenterally, e.g., by injection. Additional formulations suitable for other modes of administration include oral and pulmonary formulations, suppositories, and transdermal applications. Dosage treatment may be a single dose schedule or a multiple dose schedule. One of skill in the art can readily determine an appropriate dosage using standard dose response curves.

As will be readily appreciated by those of skill in the art after having read the present specification, the above-described methods of integrating a selected nucleotide sequence into a recipient cell genome can be practiced to treat an acquired or inherited disease in a subject. Thus, it is an even further object of the invention to provide such methods of treatment, wherein selected cells from a subject are transformed with the present nucleotide integration systems. In this manner, the Rep expression products effect the site-directed integration of a selected therapeutically-useful nucleotide sequence into the genome of the subject's cells. These methods provide for the safe and efficient integration of therapeutically useful nucleotide sequences into selected cells from a diseased host subject.

Further, the nucleotide integration systems of the present invention can be used to deliver selected sequences to a variety of cell and tissue types for the production of transgenic organisms, as well as for gene therapy, vaccination, or for characterizing a variety of genes and the mechanism of their actions. The instant methods will also find use in ribozyme and antisense therapy. For a review of antisense therapy and oligonucleotides useful in the same, see, Uhlmann, E. and Peyman, A. (1990) *Chem. Rev.* 90:543–584. For a discussion of ribozymes see, Cech et al. (1992) *J. Biol. Chem.* 267:17479–17482.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Direct Detection of Integration

In order to determine whether AAV Rep, or AAV Rep and Cap expression products are sufficient to facilitate integration of a nucleotide integration vector plasmid when transduced into a mammalian target cell, the following experiment was conducted.

1. Construction of the Cosmid pRR23

Figure 2:
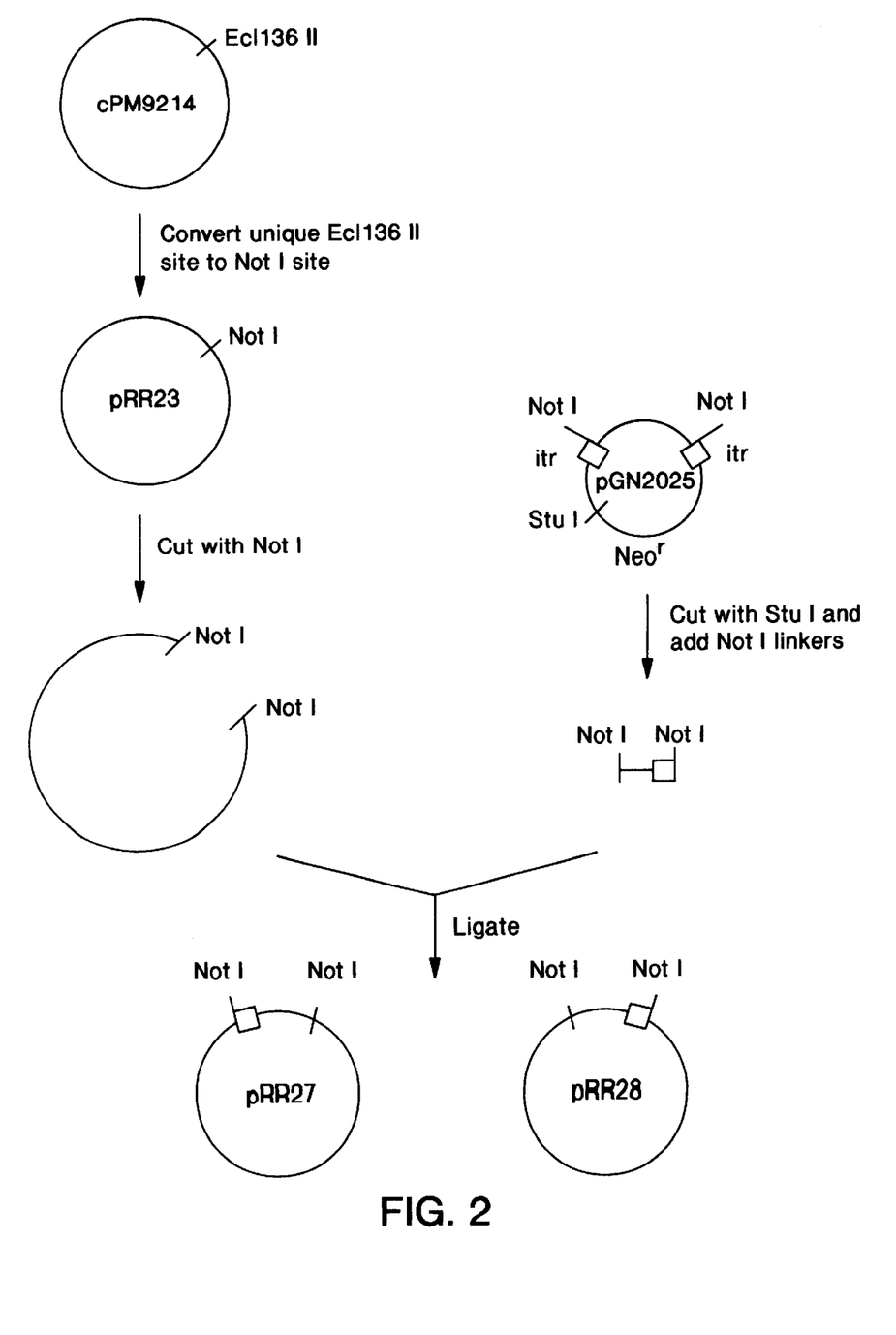
FIG. 2 depicts the assembly of cosmids pRR27 and pRR28 which were constructed by insertion of an approximately 0.6 kb fragment containing a single ITR and a portion of the neo gene into the NotI site of cosmid pRR23. Plasmids pRR27 and pRR28 contain opposite orientations of the subject 0.6 kb fragment.

Referring to FIG. 2, the cosmid pRR23 was constructed as follows. Cosmid cPM9214 (obtained from the ATCC under Accession No. 70892), which comprises approximately 28,010 base pairs of yeast DNA cloned into the BamH1 site of the vector pHC79, was restricted at the unique Ecl136I site. NotI linkers (5'-TTGCGGCCGCAA-3') (SEQ ID NO:2) were then ligated to the ends, and the resulting construct re-closed to provide cosmid pRR23 having a unique NotI site.

2. Construction of the Cosmids DRR27 and pRR28

Referring still to FIG. 2, plasmid pGN2025 that comprises the DHFR gene flanked by AAV ITRs, and further comprises the neo gene, was cut at the unique StuI site. NotI linkers (5'-TTGCGGCCGCAA-3') (SEQ ID NO:2) were then ligated to the ends, and the construct was digested with NotI to provide an approximately 0.6 kb region comprising a portion of the neo gene with a contiguous single ITR, wherein the 0.6 kb region is flanked on both sides by NotI sites. The resultant 0.6 kb fragment was then ligated into the unique NotI site of cosmid pRR23 in opposite orientations to obtain cosmids pRR27 and pRR28. Cosmids pRR27 and pRR28 thus comprise nucleotide integration vectors as defined herein due to the association of the single ITR region with a nucleotide sequence of interest (the yeast cosmid sequence) in that nucleic acid construct.

3. Transfection

A stable human cell line, 293, (readily available through, e.g., the American Type Culture Collection under Accession No. ATCC CRL1573) was grown to approximately 75% confluency in medium consisting of DMEM with 10% FBS and Pen/Strep. Approximately $10^6$ of the cultured 293 cells were transfected alone with either 1 μg of cosmids pRR27 or pRR28 (containing a single AAV ITR) using the calcium phosphate precipitation method.

Additional groups of approximately $10^6$ of the cultured 293 cells were transfected with approximately 1 μg of cosmids pRR27 or pRR28 along with 1 μg of AAV helper plasmids containing either the rep gene (pRR5) or the rep and cap genes (pGN1764), also using the calcium phosphate precipitation method. The rep containing plasmid (pRR5) included the AAV rep coding region (+145 to +2942, Srivastava et al. *J. Virol.* (1983) 45:555–564). More particularly, pRR5 was constructed as follows. All of the sequences between ApaI sites 2759 and 3862 were deleted from the AAV plasmid vector pAAVSub201 (Samulski et al. (1987) *J. Virol.* 61:3096–3101). The resultant plasmid was restricted with XbaI to yield a 3.2 kb fragment. The 3.2 kb XbaI fragment was then inserted into the SpeI site of the E3 replacement plasmid vector P680E3Δ (Ketner et al. (1994) *Proc. Natl. Acad. Sci. USA* 91:6186–6190) to yield the pRR5 construct. The rep and cap containing plasmid (pGN1764) included the same insert as pAAV-Ad (Samulski et al. *J. Virol.* (1989) 63:3822–3828) cloned in the NotI site of pBSII KS- (Stratagene). Neither plasmid included AAV ITRs.

DNA Isolation and PCR Analysis

The above-described transfected cells were passaged for approximately 2 days under suitable conditions (e.g., at 37° C. in 5% $CO_2$), then harvested and resuspended in 100 μL Phosphate buffered saline (PBS). The cells were lysed in G-DNA lysis buffer at 37° C. overnight. The DNA was then extracted with phenol/chloroform/isoamyl alcohol, and then ethanol precipitated. The final pellet was resuspended in 100 μL of Tris-EDTA buffer (TE), pH 7.5, and RNase (10 μg/ml).

If site specific integration has occurred, it should be possible to detect it by PCR, using a pair of primers, one complementary to the AAV ITR and the other complementary to a region of chromosome 19 adjacent to the preferred AAV integration site. The PCR amplified DNA would be expected to be heterogeneous, as template DNA is obtained from a pool of cells in which many independent integration reactions have occurred. Furthermore, AAV integration sites in this region are spread over several hundred base pairs. However, the PCR amplified products should contain sequences homologous to AAVS1, and therefore should hybridize to probes from this region.

PCR was carried out using 2 μL of the resultant DNA preparation and 1 μM of the oligos GN97 and GN100. The oligo GN97 is a chromosome 19 probe containing the BamHI site from AAVS1, and has the following nucleotide sequence: 5'-CGGGGAGGATCCGCTCAGAGGTACA-3' (SEQ ID NO: 3). The oligo GN100 is derived from an AAV ITR (Kotin et al. (1992) *EMBO J.* 11:5071–5078) and has the following nucleotide sequence: 5'-CGGCCTCAGTGAGCGAGCGCGC-3' (SEQ ID NO: 4). The PCR reaction also contained 1×Vent Polymerase Buffer (available from NEB) supplemented with 2 mM $MgSO_4$ and 1U deep vent exo- polymerase (available from NEB). The cycle used for the reaction was: 99° C. for 10 seconds, 72° C. for 4 minutes, repeated 35 times.

Hybridizations were then carried out as follows. The PCR products were analyzed by spotting 10 μL aliquots from the various reactions onto Zeta-probe membranes (available from Biorad) using a dot blot apparatus. The membranes were baked at 80° C. for approximately 30 minutes, and hybridized at 65° C. for approximately one hour in 1 mM EDTA, 0.25 M $Na_2HPO_4$ (pH 7.2), and 7% SDS. The probe employed was the 300-base SacI-BamHI fragment from AAVS1. This fragment was obtained using PCR with template pRVK (a vector containing AAVS1) and the primers GN79 and GN80. The primer GN79 is a chromosome 19 probe containing the SacI site from AAVS1, and has the following nucleotide sequence: 5'-ACTTTGAGCTCTACTGGCTTC-3' (SEQ ID NO: 5). The primer GN80 is a chromosome 19 probe containing the BamHI site from AAVS1 and has overlapping sequence homology with the oligo GN97. Primer GN80 has the following nucleotide sequence: 5'-GGAGGATCCGCTCAGAGG-3' (SEQ ID NO: 6). Three million cpm of the probe (Cerekov) were denatured, added to fresh phosphate buffer, and used to hybridize to the filters at 65° C. for approximately 14 hours. The filters were washed, and autoradiographed for approximately 20 hours.

A control was run using aliquots of DNA from PRVK ranging from 0 to 10 ng. The control dot blots were prepared as set forth in Table 1 below.

TABLE 1

| Control Set A, pRVK | |
|---|---|
| lane | pRVK aliquot |
| 1 | 10 ng |
| 2 | 1 ng |
| 3 | 0.1 ng |
| 4 | 0 |

Sample dot blot hybridizations of the PCR products obtained from the cultured 293 cells (that were transfected alone with either cosmids pRR27 or pRR28 (containing a single AAV ITR), or that were transfected with cosmids pRR27 or pRR28 along with AAV helper plasmids containing either the rep gene (pRR5) or the rep and cap genes (pGN1764)) were arranged as set forth in Table 2 below.

TABLE 2

| | Sample Set B | |
|---|---|---|
| lane | PCR product | Comments |
| 1 | 0 DNA | negative control |
| 2 | pAAVSub201 | positive control |
| 3 | pRR28 | 1 µg |
| 4 | pRR27 + p1764 | 1 µg + 1 µg |
| 5 | pRR27 + pRR5 | 1 µg + 1 µg |
| 6 | pRR28 + p1764 | 1 µg + 1 µg |
| 7 | pRR28 + pRR5 | 1 µg + 1 µg |

Figure 3A:
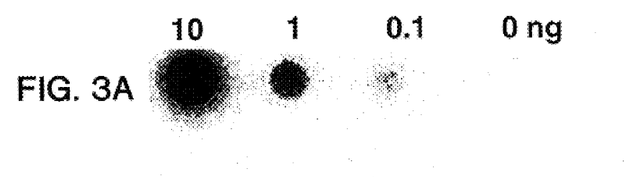
FIG. 3 depicts the results from a PCR-dot blot hybridization procedure conducted to detect rep-mediated site specific integration of plasmids carrying a target sequence (homologous to an AAV ITR) into the genomic DNA of 293 cells.
Figure 3B:
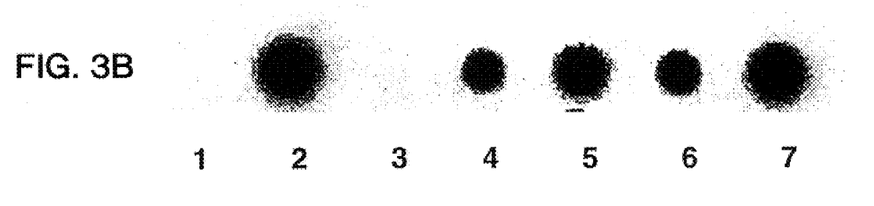

Referring to FIG. 3, wherein the results of the control and sample dot blot hybridizations are depicted, it is clear that both pRR27 and pRR28 were successfully integrated site-specifically into the 293 cell genomes, both in the presence of the AAV Rep expression products and in the presence of the AAV Rep and Cap expression products.

Thus, novel nucleotide sequence integration systems are disclosed, as are methods of making and using the same. Although preferred embodiments of the subject invention have been described in some detail, it is understood that obvious variations can be made without departing from the spirit and the scope of the invention as defined by the appended claims.

What is claimed is:

1. An integration system for inserting a selected nucleotide sequence into a suitable recipient cell genome, said system comprising the combination of:
   (a) a vector comprising a nucleic acid construct having (i) a single targeting sequence containing an AAV Rep binding site that binds AAV Rep and wherein said single targeting sequence comprises at least one GCTC sequence and is 145 bases or less in length and (ii) a heterologous nucleotide sequence arranged relative to the targeting sequence such that said targeting sequence directs integration of the heterologous nucleotide sequence into the recipient cell genome; and
   (b) Rep expression products, wherein said Rep expression products effect integration of the heterologous nucleotide sequence from said vector into the recipient cell genome.

2. The integration system of claim 1, wherein said Rep expression products are provided by a second nucleic acid construct comprising an AAV rep coding region operably linked to control elements that direct the transcription and translation of said rep coding region in the recipient cell to provide said rep translation products.

3. The integration system of claim 1, wherein the vector comprises a circular piece of DNA.

4. The integration system of claim 1, wherein the targeting sequence is a single inverted terminal repeat (ITR) sequence.

5. The integration system of claim 4, wherein the targeting sequence comprises a 145 base pair (bp) ITR sequence as depicted in FIG. 1 (SEQ ID NO: 1).

6. The integration system of claim 4, wherein said Rep expression products are provided by a second nucleic acid construct, comprising an AAV rep coding region operably linked to control elements that direct the transcription and translation of said rep coding region in the recipient cell, thereby providing rep translation products that effect integration of the heterologous nucleotide sequence into the recipient cell genome.

7. The integration system of claim 4, wherein the vector comprises a circular piece of DNA.

8. A method of integrating a selected nucleotide sequence into a recipient cell genome, said method comprising the steps:
   (a) introducing a first nucleic acid construct into the recipient cell, said first construct comprising a single targeting sequence which contains an AAV Rep binding site that binds AAV Rep and wherein said single targeting sequence comprises at least one GCTC sequence and is 145 bases or less in length, and a selected heterologous nucleotide sequence suitably arranged in the first construct relative to the targeting sequence such that the targeting sequence directs integration of said heterologous sequence into a target site in the recipient cell genome; and
   (b) introducing Rep expression products into the recipient cell, whereby said Rep expression products effect integration of the selected heterologous nucleotide sequence from the first nucleic acid construct into the recipient cell genome.

9. The method of claim 8, wherein step (b) comprises introducing a second nucleic acid construct into the recipient cell, said second construct comprising an AAV rep coding region operably linked to control elements that direct the transcription and translation of said rep coding region in the recipient cell, thereby providing rep translation products that effect integration of the selected heterologous nucleotide sequence from the first nucleic acid construct into the recipient cell genome.

10. The method of claim 8, wherein the targeting sequence is a wild type (wt) AAV ITR sequence.

11. The method of claim 10, wherein the heterologous nucleotide sequence comprises a coding region that encodes a polypeptide, said coding region operably linked to control elements that direct the transcription and translation thereof in the recipient cell.

12. The method of claim 11, wherein the targeting sequence directs integration of the heterologous nucleotide sequence into chromosome 19 of the recipient cell genome.

13. The method of claim 12, wherein the heterologous nucleotide sequence comprises a coding region that encodes a protein defective or missing from the recipient cell genome.

14. A method of integrating a selected nucleotide sequence into a recipient cell genome, comprising introducing the integration system of claim 1 into a suitable recipient cell.

15. A method of integrating a selected nucleotide sequence into a recipient cell genome, comprising introducing the integration system of claim 2 into a suitable recipient cell.

16. A method of integrating a selected nucleotide sequence into a recipient cell genome, comprising introducing the integration system of claim 4 into a suitable recipient cell.

17. A method of integrating a selected nucleotide sequence into a recipient cell genome, comprising introducing the integration system of claim 6 into a suitable recipient cell.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 145 base pairs
      (B) TYPE: nucleic acid
      (C) STRANDEDNESS: single
      (D) TOPOLOGY: linear    (xi) SEQUENCE DESCRIPTION: SEQ ID NO:1:

```
TTGGCCACTC CCTCTCTGCG CGCTCGCTCG CTCACTGAGG CCGCCCGGGC AAAGCCCGGG      60

CGTCGGGCGA CCTTTGGTCG CCCGGCCTCA GTGAGCGAGC GAGCGCGCAG AGAGGGAGTG     120

GCCAACTCCA TCACTAGGGG TTCCT                                          145
```

(2) INFORMATION FOR SEQ ID NO:2:

(i) SEQUENCE CHARACTERISTICS:
      (A) LENGTH: 12 base pairs
      (B) TYPE: nucleic acid
      (C) STRANDEDNESS: single
      (D) TOPOLOGY: linear    (xi) SEQUENCE DESCRIPTION: SEQ ID NO:2:

```
TTGCGGCCGC AA                                                         12
```

(2) INFORMATION FOR SEQ ID NO:3:

(i) SEQUENCE CHARACTERISTICS:
      (A) LENGTH: 25 base pairs
      (B) TYPE: nucleic acid
      (C) STRANDEDNESS: single
      (D) TOPOLOGY: linear    (xi) SEQUENCE DESCRIPTION: SEQ ID NO:3:

```
CGGGGAGGAT CCGCTCAGAG GTACA                                           25
```

(2) INFORMATION FOR SEQ ID NO:4:

(i) SEQUENCE CHARACTERISTICS:
      (A) LENGTH: 22 base pairs -continued

```
            (B) TYPE: nucleic acid
            (C) STRANDEDNESS: single
            (D) TOPOLOGY: linear (xi) SEQUENCE DESCRIPTION: SEQ ID NO:4:

CGGCCTCAGT GAGCGAGCGC GC                                                    22

(2) INFORMATION FOR SEQ ID NO:5:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:5:

ACTTTGAGCT CTACTGGCTT C                                                     21

(2) INFORMATION FOR SEQ ID NO:6:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:6:

GGAGGATCCG CTCAGAGG                                                         18
```